(12) United States Patent
Dufour et al.

(10) Patent No.: US 10,729,410 B2
(45) Date of Patent: Aug. 4, 2020

(54) FEATURE-BASED CALIBRATION OF ULTRASOUND IMAGING SYSTEMS

(71) Applicant: KONINKLIJKE PHILIPS N.V., Eindhoven (NL)

(72) Inventors: Cecile Dufour, Paris (FR); Benoit Jean-Dominique Bertrand Maurice Mory, Mercer Island, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 240 days.

(21) Appl. No.: 15/314,964

(22) PCT Filed: Jun. 18, 2015

(86) PCT No.: PCT/EP2015/063721
§ 371 (c)(1),
(2) Date: Nov. 30, 2016

(87) PCT Pub. No.: WO2015/193441
PCT Pub. Date: Dec. 23, 2015

(65) Prior Publication Data
US 2017/0196540 A1 Jul. 13, 2017

(30) Foreign Application Priority Data
Jun. 18, 2014 (EP) .................................... 14305929

(51) Int. Cl.
*A61B 8/00* (2006.01)
*A61B 8/08* (2006.01)
(Continued)

(52) U.S. Cl.
CPC .......... *A61B 8/5215* (2013.01); *A61B 6/4417* (2013.01); *A61B 8/0891* (2013.01);
(Continued)

(58) Field of Classification Search
CPC ... A61B 8/5215; A61B 8/0891; A61B 6/4417; A61B 8/463; A61B 8/466; A61B 8/58;
(Continued)

(56) References Cited

U.S. PATENT DOCUMENTS 5,949,491 A * 9/1999 Callahan ................. G01S 7/003
348/442
9,524,551 B2 12/2016 Hashimoto et al.
(Continued)

FOREIGN PATENT DOCUMENTS

WO 2012117381 A1 9/2012
WO 2013001410 A2 1/2013
(Continued)

OTHER PUBLICATIONS

C. Cunningham, "Picture archival and communications system (PACS) and the ultrasound department," Feb. 2005, Ultrasound, vol. 13, No. 1, pp. 12-16.*

(Continued)

*Primary Examiner* — Joel Lamprecht (57) ABSTRACT

An ultrasound imaging apparatus is disclosed for identifying anatomical objects in a field of view. The apparatus comprises an image interface for receiving 3D medical image data of a patient, and a segmentation unit for segmenting anatomical objects of the patient in the 3D medical image data and for providing segmentation data of the anatomical objects. An ultrasound acquisition unit including an ultrasound probe is included for acquiring ultrasound data of the patient. The apparatus further comprises a position determining unit for determining a position of the ultrasound probe, wherein the position determining unit includes a calibration unit for calibrating the position of the ultrasound probe on the basis of anatomical features of the patient. An identification unit is included in the apparatus for identifying the anatomical objects within the field of view of the (Continued)

ultrasound probe on the basis of the segmentation data and the position of the ultrasound probe.

22 Claims, 8 Drawing Sheets

(51) Int. Cl.
  *G06T 7/11* (2017.01)
  *A61B 6/00* (2006.01)
  *G06T 7/00* (2017.01)
(52) U.S. Cl.
  CPC .......... *A61B 8/4245* (2013.01); *A61B 8/463* (2013.01); *A61B 8/466* (2013.01); *A61B 8/483* (2013.01); *A61B 8/5261* (2013.01); *A61B 8/58* (2013.01); *G06T 7/11* (2017.01); *A61B 8/08* (2013.01); *G06K 2209/057* (2013.01); *G06T 7/0012* (2013.01); *G06T 2207/10136* (2013.01)
(58) Field of Classification Search
  CPC ..... A61B 8/4245; A61B 8/5261; A61B 8/483; A61B 8/08; G06T 7/11; G06T 7/0012; G06T 2207/10136; G06K 2209/057
  USPC ........................................................ 600/437
  See application file for complete search history.

(56) References Cited

U.S. PATENT DOCUMENTS

| | | | |
|---|---|---|---|
| 2009/0124906 A1 | 5/2009 | Caluser | |
| 2010/0286517 A1* | 11/2010 | Kamen | A61B 10/0241 600/438 |
| 2011/0026796 A1 | 2/2011 | Hyun et al. | |
| 2011/0172526 A1* | 7/2011 | Lachaine | A61B 34/20 600/439 |
| 2012/0253200 A1* | 10/2012 | Stolka | A61B 1/041 600/459 |
| 2012/0287131 A1 | 11/2012 | Matsuzaki et al. | |
| 2013/0053679 A1* | 2/2013 | Owen | A61B 6/032 600/411 |
| 2013/0182924 A1* | 7/2013 | Lause | G06T 7/0014 382/131 |
| 2013/0266178 A1* | 10/2013 | Jain | G06T 7/70 382/103 |
| 2013/0279780 A1* | 10/2013 | Grbic | A61B 5/0033 382/131 |
| 2014/0193053 A1* | 7/2014 | Kadoury | G06T 11/008 382/131 |
| 2016/0007970 A1* | 1/2016 | Dufour | A61B 8/4254 600/437 |
| 2016/0113632 A1* | 4/2016 | Ribes | A61B 8/0891 600/440 |

FOREIGN PATENT DOCUMENTS

| | | |
|---|---|---|
| WO | 2013132402 A2 | 9/2013 |
| WO | 2013136278 A1 | 9/2013 |

OTHER PUBLICATIONS

A. Fenster, D. B. Downey, and H. N. Cardinal, "Three-dimensional ultrasound imaging," 2001, Phys. Med. Biol., vol. 46., pp. R67-R99.*
J. A. Noble et al., "Ultrasound image segmentation: a survey," Aug. 2006, IEEE Transactions on Medical Imaging, vol. 25, No. 8, pp. 987-1010.*
J. A. Noble et al., "Ultrasonic image analysis and image-guide interventions," 2011, Interface Focus, vol. 1, pp. 673-685.*
R. W. Prager et a;,, "Three-dimensional ultrasound imaging," Feb. 2010, Proceedings of the Institution of Mechanical Engineers, Part H: Journal of Engineering in Medicine, vol. 224, No. 2, pp. 193-223.*
Pizaine et al., "Implicit medial representation for vessel segmentation," Mar. 2011, Proc. SPIE 7962, Medical Imaging 2011: Image Processing, vol. 79623Q, pp. 79623Q-1-79623Q-7.*
J. Powers et al., "Medical ultrasound systems," 2011, Interface Focus, vol. 1, pp. 477-489.*
Ji et al., "Mutual-information-based image to patient re-registration using intraoperative ultrasound in image-guided neurosurgery," Oct. 2008, Medical Physics, vol. 35, No. 10, pp. 4612-4624.*
Reinertsen et al., "Intra-operative correction of brain-shift," 2014, Published online Apr. 3, 2014, Acta. Neurochir. vol. 156, pp. 1301-1310.*
Hsu et al., "Freehand 3D ultrasound calibration: A review," 2009, In Advanced imaging in biology and medicine (Eds Sensen, C. W., and Hallgrimsson, B.), ch. 3, pp. 47-84 (Springer-Verlag Berlin).*
Lange et al., "Augmenting intraoperative 3D ultrasound with pre-operative models for navigation in liver surgery," 2004, In Proc. Medical Image Computing and Computer-Assisted Intervention-MICCAI 2004, vol. 3217, pp. 534-541.*
Lee, "Fusion imaging of real-time ultrasonography with CT or MRI for hepatic intervention," 2014, Published online Jun. 10, 2014, Ultrasonography, vol. 33, No. 4, pp. 227-239.*
Suzuki, "Pixel-Based machine learning in medical imaging," 2012, International Journal of Biomedical Imaging, vol. 2012, Article ID 792079.*
Hakime, et al., "Clinical Evaluation of Spatial Accuracy of a Fusion Imaging Technique Combining Previously Acquired Computed Tomography and Real-Time Ultrasound for Imaging of Liver Metastases", Cardiovascular and Interventional Radiological Society of Europe, published Sep. 16, 2010.

* cited by examiner

FEATURE-BASED CALIBRATION OF ULTRASOUND IMAGING SYSTEMS

This application is the U.S. National Phase application under 35 U.S.C. § 371 of International Application No. PCT/EP2015/063721, filed on Jun. 18, 2015, which claims the benefit of European Application Serial No. 14305929.3, filed Jun. 18, 2014. These applications are hereby incorporated by reference herein.

FIELD OF THE INVENTION

The present invention relates to an ultrasound imaging apparatus for identifying anatomical objects in a field of view. The present invention further relates to a method for identifying anatomical objects in a field of view of an ultrasound acquisition unit and to a computer program comprising program means for causing a computer to carry out the steps of the method according to the invention when said computer program is carried out on a computer.

BACKGROUND OF THE INVENTION

In the field of medical imaging systems it is generally known to combine different images of a patient acquired by different medical analysis systems in order to improve the diagnostic possibilities. In particular, ultrasound systems are known which combine ultrasound images and pre-operative image data of a patient derived from a different imaging system. The ultrasound system is provided with a probe position tracking system to determine the position of the ultrasound probe at the patient's body to correlate the corresponding ultrasound images with the pre-operative volume analysis data. The positioning system enables a continuous spatial alignment of the pre-operative data and the live ultrasound data.

The position tracking systems rely on a calibration based e.g. on artificial markers which can be identified in the pre-operative and the ultrasound data and which can be correlated to each other so that the alignment of the data can be determined. The position tracking system may also comprise an electromagnetic tracking system which determines an offset between a sensor coordinate system and an ultrasound coordinate system. Such a probe positioning system is e.g. known from WO 2012/117381 A1.

The probe positioning systems usually have a high accuracy in the vicinity of the markers, however, the accuracy is reduced if the probe is moved away from the markers. Further, if a misalignment between the pre-operative data and the ultrasound data occurs, a manual readjustment is necessary, which is time-consuming and requires detailed expert knowledge.

SUMMARY OF THE INVENTION

It is therefore an object of the invention to provide an improved ultrasound imaging apparatus and an improved method for identifying anatomical objects in a field of view of an ultrasound probe with low technical effort and reduced time consumption.

According to one aspect an ultrasound imaging apparatus for identifying anatomical objects in a field of view is provided, comprising:
an image interface for receiving 3D medical image data of a patient,
a segmentation unit for segmenting anatomical objects of the patient in the 3D medical image data and for providing segmentation data of the anatomical objects,
an ultrasound acquisition unit including an ultrasound probe for acquiring ultrasound data of the patient,
a position determining unit for determining a position of the ultrasound probe, wherein the position determining unit includes a calibration unit for calibrating the position of the ultrasound probe on the basis of anatomical features of the patient, and
an identification unit for identifying the anatomical objects within the field of view of the ultrasound probe on the basis of the segmentation data and the position of the probe.

According to another aspect a method for identifying anatomical objects in a field of view of an ultrasound acquisition unit is provided, comprising the steps of:
receiving 3D medical image data of a patient,
segmenting anatomical objects in the 3D medical image data and providing segmentation data of the anatomical features,
acquiring ultrasound data of the patient by means of an ultrasound probe of the ultrasound acquisition unit,
calibrating a position of the ultrasound probe on the basis of anatomical features of the patient,
determining a position of the ultrasound probe on the basis of the calibrated position of the ultrasound probe, and
identifying the anatomical objects within the field of view on the basis of the segmentation data and the position of the probe.

According to another aspect a computer program is provided comprising program code means for causing a computer to carry out the steps of the method according to the invention when said computer program is carried out on a computer.

Preferred embodiments of the invention are defined in the dependent claims. It shall be understood that the claimed method has similar and/or identical preferred embodiments as the claimed device and as defined in the dependent claims.

The present invention is based on the idea to synchronize pre-operative image data of a patient with ultrasound image data of the patient in order to improve the identification of objects in the field of view. The ultrasound image data and the pre-operative image data are synchronized on the basis of segmented anatomical features of the pre-operative image data and a position of the ultrasound probe. The position of the ultrasound probe with respect to the segmented pre-operative image data is calibrated on the basis of anatomical features of the patient in order to achieve a precise correlation and a precise identification of objects like organs in the field of view of the ultrasound probe. Since the positioning unit is calibrated on the basis of anatomical features like vessels of the liver, the position of the ultrasound acquisition unit can be determined precisely with low technical effort.

In a preferred embodiment, the ultrasound acquisition unit is adapted to determine 3D ultrasound data. This is a possibility to provide detailed ultrasound data of the anatomical objects and the anatomical features in order to achieve a precise identification in the field of view.

In a further preferred embodiment, the identification unit is adapted to identify the identical objects on the basis of a correlation of anatomical features in the 3D medical image data and the 3D ultrasound data. This is a possibility to improve the reliability of the identification of the anatomical objects, since the correlation is performed on the basis of the three-dimensional shape of the objects.

In a preferred embodiment, the calibration unit is adapted to calibrate the position determining unit on the basis of a correlation of the anatomical features in the 3D medical image data and the 3D ultrasound data. This is a possibility to achieve a precise calibration of the position determining unit, since the 3D medical image data including the segmentation data of the anatomical objects is correlated to the corresponding 3D ultrasound data acquired at the current position of the ultrasound probe.

In a preferred embodiment, the 3D ultrasound data is segmented to provide ultrasound segmentation data of the anatomical features of the patient and the calibration unit is adapted to calibrate the position of the ultrasound probe on the basis of a correlation of the segmentation data and the ultrasound segmentation data. This is a possibility to achieve an automatic calibration merely on the basis of a 3D medical image data and the 3D ultrasound data.

In a preferred embodiment, the anatomical features are organs of the patient. This is a possibility to achieve a precise calibration, since the organs can be segmented in the ultrasound data and the 3D medical image data with low technical effort.

It is further preferred if the anatomical features are portions of the organs of the patient, in particular vessels of the organs of the patient. This is a possibility to further improve the reliability of the calibration, since the portions of the organs and in particular the vessels of the organs can be identified with high precision and have a characteristic structure, so that the reliability can be improved.

In a preferred embodiment, the ultrasound imaging apparatus further comprises a display unit for displaying a 2D representation of the ultrasound data and of the segmentation data. This is a possibility to improve the visibility of the identified anatomical objects, since the anatomical objects can be easily identified on the basis of the segmentation data.

In a preferred embodiment, the identified organs are displayed by the display unit and labeled on the basis of the segmentation data. This is a possibility to further improve the comfort of the system, since an operator does not need to identify the organs on the basis of their anatomical shape.

In a preferred embodiment, the calibration unit is adapted to calibrate the position of the ultrasound probe on the basis of the anatomical features upon request of an operator. This is a possibility to realign the segmentation data and the ultrasound data if a misalignment occurs.

In a preferred embodiment, the calibration unit is adapted to calibrate the position of the ultrasound probe on the basis of the anatomical features when a misalignment is detected. This is a possibility to achieve an automatic realignment of the segmentation data and the ultrasound data.

In a preferred embodiment, the acquired 3D ultrasound data comprises a plurality of 3D voxels, wherein the 3D voxels are assigned to the corresponding anatomical objects of the segmentation data. This is a possibility to easily identify the anatomical object in the field of view of the ultrasound acquisition unit, since each 3D voxel is correlated to the identified anatomical objects in the segmentation data so that the anatomical objects can be easily identified below technical effort.

In a preferred embodiment, an anatomical object is identified in the field of view on the basis of an amount of 3D voxels of the anatomical objects in the field of view. This is a possibility to identify the anatomical object in the field of view with low technical effort.

In a preferred embodiment, the ultrasound acquisition unit is adapted to determine 2D ultrasound data. This is a possibility to reduce the technical effort for acquiring the ultrasound data.

In a preferred embodiment, the acquired 2D ultrasound data comprises a plurality of 2D pixels assigned to the corresponding anatomical objects of the segmentation data, wherein the anatomical object in the field of view is identified on the basis of an amount of 2D pixels of the anatomical objects in the field of view. This is a possibility to further reduce the technical effort for identifying the anatomical object in the field of view, since the amount of assigned 2D pixels can be easily determined.

As mentioned above, the anatomical objects in the field of view are identified on the basis of the correlation of the segmentation data and the position of the ultrasound probe, wherein the position of the ultrasound probe is easily and precisely calibrated on the basis of anatomical features in the ultrasound data and the corresponding segmentation data of the 3D medical image data. Since the anatomical features can be automatically detected in the medical image data and the ultrasound image data by image processing such as image segmentation, the calibration and the respective determination of the position of the ultrasound probe can be achieved with high precision so that the identification of the anatomical objects can be achieved with a high reliability. In order to reduce the technical effort, the anatomical objects in the field of view are identified by 3D voxels or 2D pixels assigned to the respective anatomical objects on the basis of the segmentation data and the position of the ultrasound probe so that the anatomical object in the field of view can be identified with low technical effort by determining the amount of 3D voxels or 2D pixels, respectively. Consequently, a precise identification of anatomical objects in the field of view of the ultrasound probe can be achieved with low technical effort.

BRIEF DESCRIPTION OF THE DRAWINGS

These and other aspects of the invention will be apparent from and elucidated with reference to the embodiment(s) described hereinafter. In the following drawings

FIGS. 2a, b, c show drawings of pre-operative images of a volume of the patient's body including segmentations of anatomical objects;

FIGS. 3a, b show segmentation data of the pre-operative images and the position of the ultrasound probe;

FIGS. 4a, b show an ultrasound image and a pre-operative image of the same region of the patient's body for calibration of the positioning unit;

FIGS. 5a, b show a pre-operative image and correlated segmentation data of the pre-operative image of the same region of the patient's body in 2D and 3D;

FIGS. 6 a, b show a pre-operative image and a corresponding ultrasound image for illustrating an alignment of the segmentation data and the anatomical features in the ultrasound image;

FIGS. 7 a, b show a pre-operative image and an ultrasound image and correlated segmentation data of the same region for illustrating a misalignment.

DETAILED DESCRIPTION OF THE INVENTION

Figure 1:
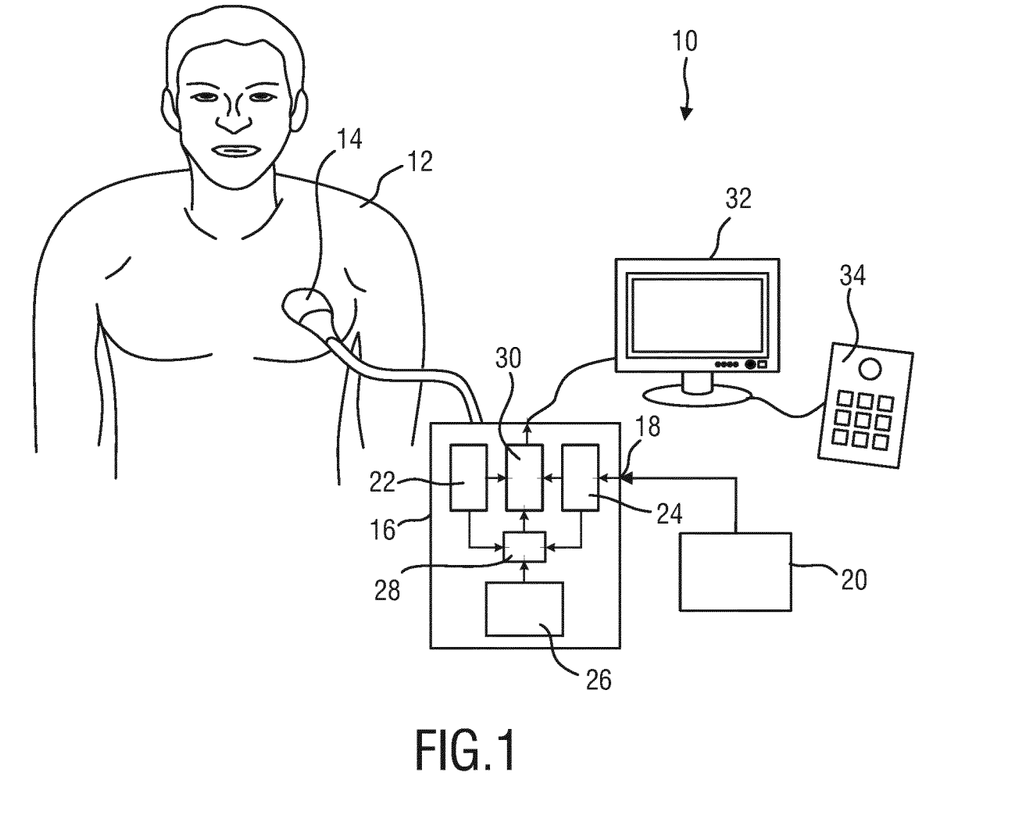
FIG. 1 shows a schematic representation of a medical imaging system in use to scan a volume of a patient's body.

FIG. 1 shows a schematic illustration of a medical imaging system 10 according to one embodiment, in particular an ultrasound imaging system 10. The medical imaging system 10 is applied to inspect a volume of an anatomical site, in particular an anatomical site of a patient 12. The medical imaging system 10 comprises an ultrasound probe 14 having at least one transducer array including a multitude of transducer elements for transmitting and receiving ultrasound waves. The transducer elements are preferably arranged in a 2D array, in particular for providing multi dimensional image data.

The medical imaging system 10 comprises in general an image processing apparatus 16 for evaluating the ultrasound data received from the ultrasound probe 14 and for combining or correlating the ultrasound images with pre-operative images of the patient 12. The image processing apparatus 16 comprises an image interface 18 for receiving the pre-operative image data from an external database 20 or an external analysis and imaging apparatus 20. The pre-operative image data is preferably computer tomography image data or magnetic resonance tomography image data which has been captured or acquired prior to the ultrasound imaging analysis by a computer tomography apparatus or a magnetic resonance tomography apparatus. The image processing apparatus 16 comprises an image evaluation unit 22 connected to the ultrasound probe 14 for evaluating the ultrasound data and for providing ultrasound image data from the volume or object of the patient 12 which is analyzed by the ultrasound probe 14. The image processing apparatus 16 further comprises a segmentation unit 24, which is connected to the image interface 18 for receiving the pre-operative image data from the external imaging apparatus 20 or the database 20 and for segmenting the image data in order to provide 3D data of anatomical features of the patient 12, in particular segmentation data of the different organs within the body of a patient 12.

The ultrasound imaging apparatus 10 further comprises a position determining unit 26 for determining a position of the ultrasound probe 14. The position determining unit 26 determines the relative position of the ultrasound probe e.g. by means of electromagnetic tracking in order to determine a movement of the ultrasound 14 with respect to an initial or a calibrated position. The initial position is calibrated by means of a calibration unit 28. The calibration unit 28 is connected to the image evaluation unit 22, the segmentation unit 24 and to the position determining unit 26 in order to correlate the ultrasound data captured by the ultrasound probe 14, the segmentation data and the position of the ultrasound probe 14 determined by means of the position determining unit 26. The calibration unit 28 correlates anatomical features within the ultrasound data and the segmentation data in order to determine the position of the ultrasound probe 14 with respect to the segmentation data. The so determined position of the ultrasound probe 14 with respect to the segmented anatomical features is stored and used as reference position or used as calibrated position of the ultrasound probe 14. If the ultrasound probe 14 is moved with respect to the calibrated position, the position determining unit 26 detects the distance and the direction with respect to the calibrated position and provides the so determined current position of the ultrasound probe 14.

The image processing apparatus 16 further comprises an identification unit 30 for identifying the anatomical objects within the field of view of the ultrasound probe 14. The identification unit 30 is connected to the image evaluation unit 22, the segmentation unit 24 and to the position determining unit 26. The identification unit 30 is adapted to identify the anatomical objects of the patient 12 in the field of view of the ultrasound probe 14 on the basis of the current position of the ultrasound probe 14 with respect to the calibrated position received from the position determining unit 26 and on the basis of the segmentation data received from the segmentation unit 24 including the respectively segmented anatomical objects of the patient 12, i.e. the organs of the patient 12. Since the position of the ultrasound probe 14 can be easily determined by means of the position determining unit 26 relative to the precisely calibrated position, the anatomical objects in the field of view of the ultrasound probe 14 can be easily determined with a high reliability.

The anatomical objects identified in the ultrasound data are e.g. superposed with the segmentation data received from the segmentation unit 24 and provided as a superposed image to a display unit 32 for displaying the ultrasound data. The medical imaging system 10 further comprises an input device 34 which may be connected to the display unit 32 or to the image processing apparatus 16 in order to control the image acquisition, the identification of the anatomical object and/or the display of the images and the segmentation results.

Figure 2:
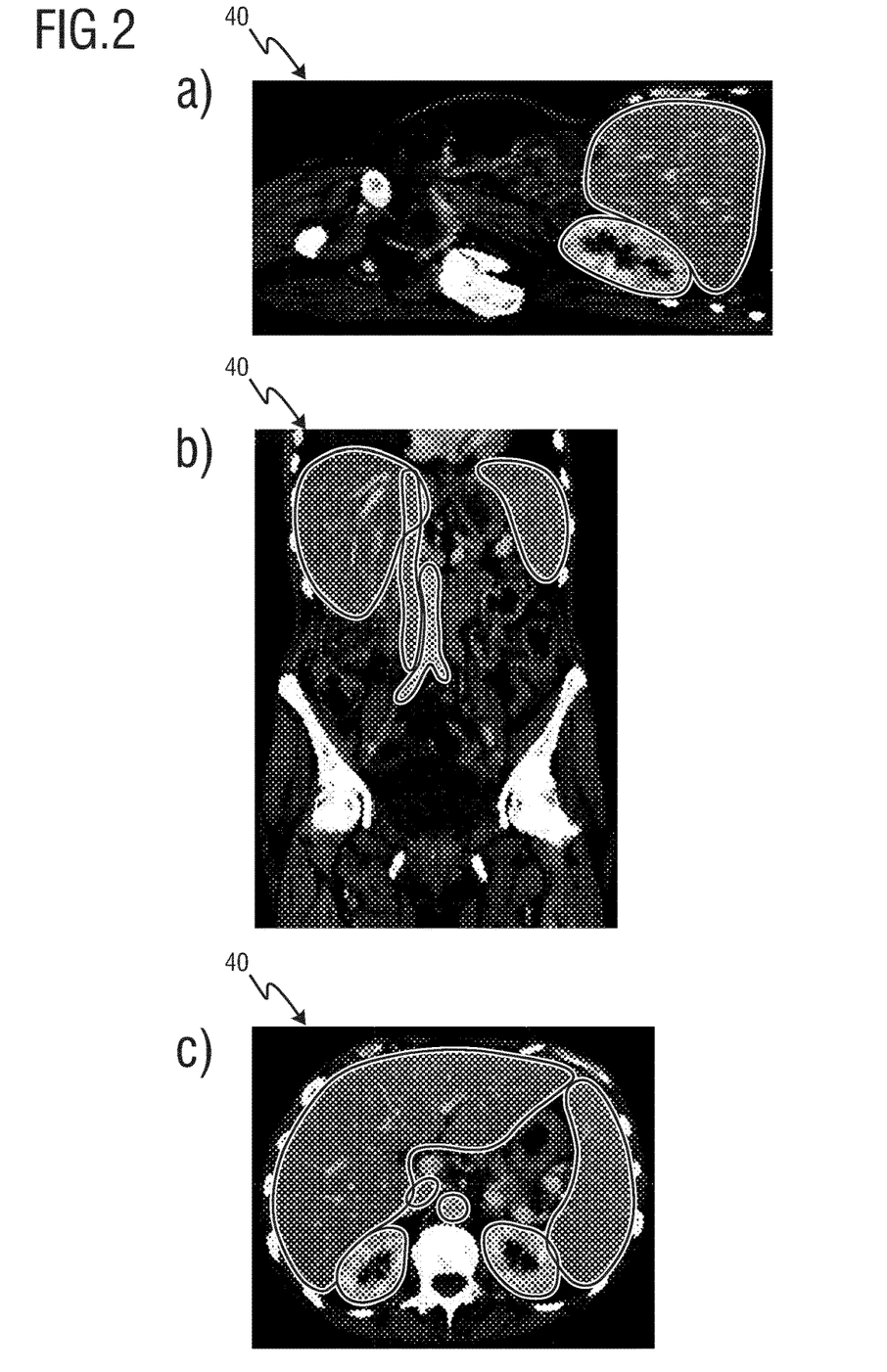

FIG. 2 shows three different two-dimensional slices of three-dimensional medical image data including segmented organs which are segmented by means of the segmentation unit 24. The 3D medial image data is generally denoted by 40 and provided by the imaging apparatus 20 or the external data base 20 shown in FIG. 1. The 3D medical image data 40 is in this case computer tomography (CT) image data captured from the patient 12. In an alternative embodiment, the 3D medical image data 40 can be magnet resonance tomography (MRT) data or other three-dimensional analysis data of the patient 12. In FIG. 2a a sagittal view including the liver and the right kidney is shown, in FIG. 2b a coronal view including the liver, the spleen, and the aorta is shown, and in FIG. 2c an axial view including the liver, the kidneys, the spleen and the aorta is shown.

The 3D medical image data 40 is segmented by means of the segmentation unit 24, i.e. the anatomical objects within the patients body are identified and the outer shape and in particular certain anatomical features like the vessels within the organs are determined by image processing and stored as three-dimensional segmentation data e.g. as 3D coordinates or the like. In FIG. 2, the two-dimensional slices of the 3D medical image data 40 and the segmentation data are shown in a superposed manner, so that the segmented organs can be identified by the outer shape displayed in the two-dimensional slices of FIG. 2a-c.

The three-dimensional medical image data 40 is usually captured prior to an operation or an ultrasound analysis so that the different organs of the patient 12 can be identified automatically or manually since the shape and the position of the organs within the patient's body are well known.

Figure 3:
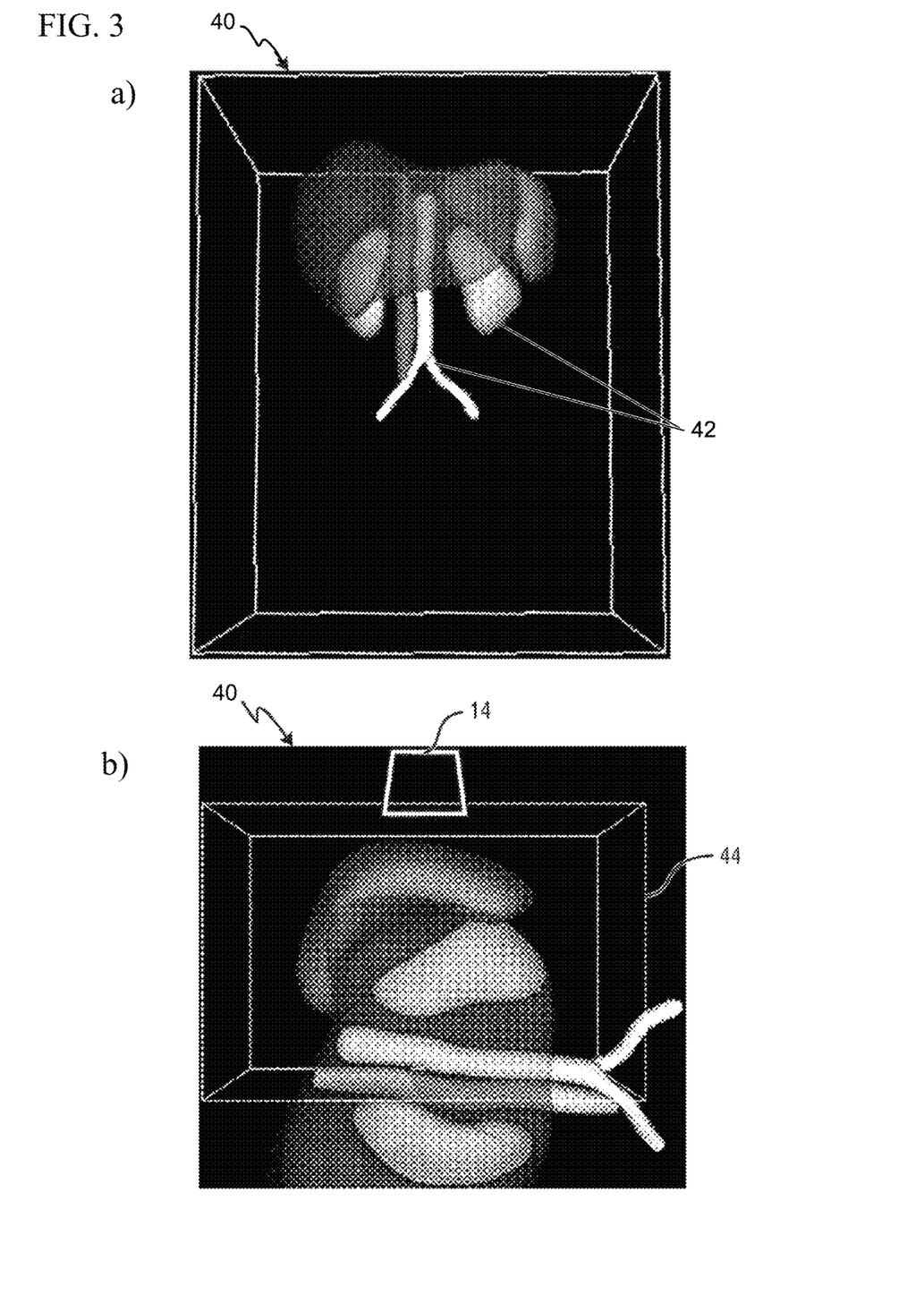

FIG. 3a, b show the three-dimensional segmentation data of the organs of the patient 12 derived from the three-dimensional image data 40 shown in FIG. 2. The segmentation data of the organs are generally denoted by 42.

As shown in FIG. 3a, the segmentation data 42 comprises certain anatomical features of the patient 12 including the outer shape of the organs, the special position of the organs and, further, additional anatomical features of the organs like internal vessels or the like.

In FIG. 3b, the relative position of the ultrasound probe 14 with respect to the organs in the segmentation data 42 is schematically shown. Further, a field of view of the ultrasound probe 14 is shown as a simplified square and generally denoted by 44. On the basis of the known position of the ultrasound probe 14 with respect to the anatomical objects in the field of view 44 of the ultrasound probe 14 can be easily identified with a high reliability.

The position of the ultrasound probe 14 is determined by means of the position determining unit 26 and calibrated by means of the calibration unit on the basis of a correlation of anatomical features in the ultrasound data and the segmentation data 42 as described in the following.

Figure 4:
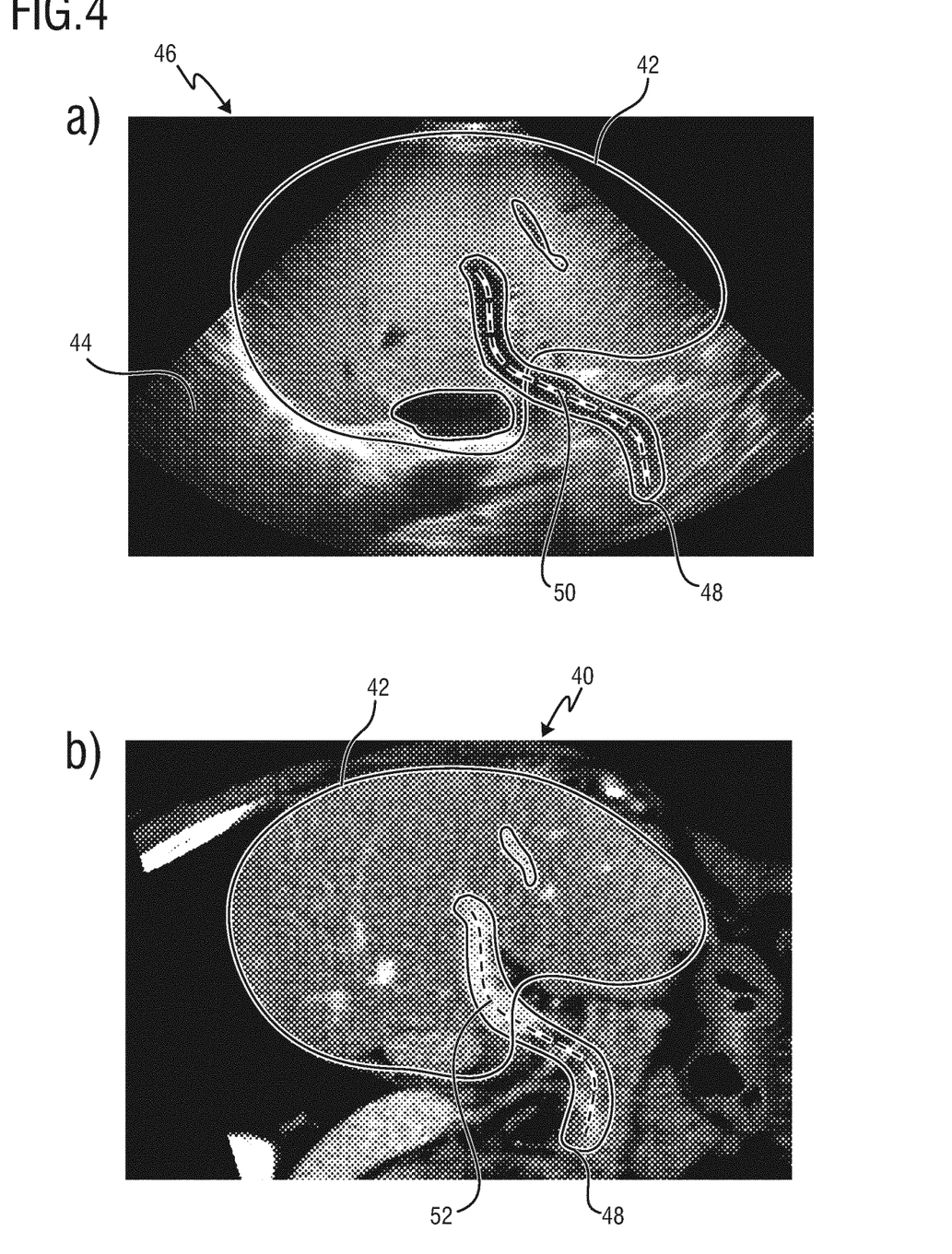

In FIG. 4*a, b* an ultrasound image and an image of the three-dimensional medical image data 40 of the same portion of the liver is schematically shown in order to explain the calibration of the position determining unit 26 on the basis of anatomical features within the ultrasound data and the three-dimensional medical image data 40.

In general, certain anatomical features like vessels are identified in ultrasound image data 46 shown in FIG. 4*a* and in the 3D medical image data 40 shown in FIG. 4*b* by means of segmentation so that the position of the ultrasound probe 14 with respect to the anatomical objects in the segmentation data 42 can be determined and used for the calibration of the position determining unit 26.

In detail the anatomical object shown in FIGS. 4*a* and *b* is the identical view in the ultrasound image data 46 and in the 3D medical image data 40 of the liver of the patient 12. As shown in FIGS. 4*a* and *b*, vessels 48 of the liver are identified in the ultrasound image data 46 and the 3D medical image data 40 as the anatomical features and used for the calibration of the positioning unit 26. The image data 40, 46 are both segmented in order to identify the vessels 48 as the anatomical features. During the segmentation center lines 50, 52 of the vessels 48 in the ultrasound image data 46 and the 3D medical image data 40 are extracted and used for the respective correlation. On the basis of the so extracted center lines 50, 52 a correlation of the vessels 48 in the different images can be performed with high precision and high reliability so that the position of the probe 14 can be determined with respect to the segmentation data 42 of the 3D medical image data 40 and calibrated.

The so calibrated position determining unit 26 can be used for identifying the organs of the patient 12 as the anatomical objects within the field of view 44 of the ultrasound probe 14.

Figure 5:
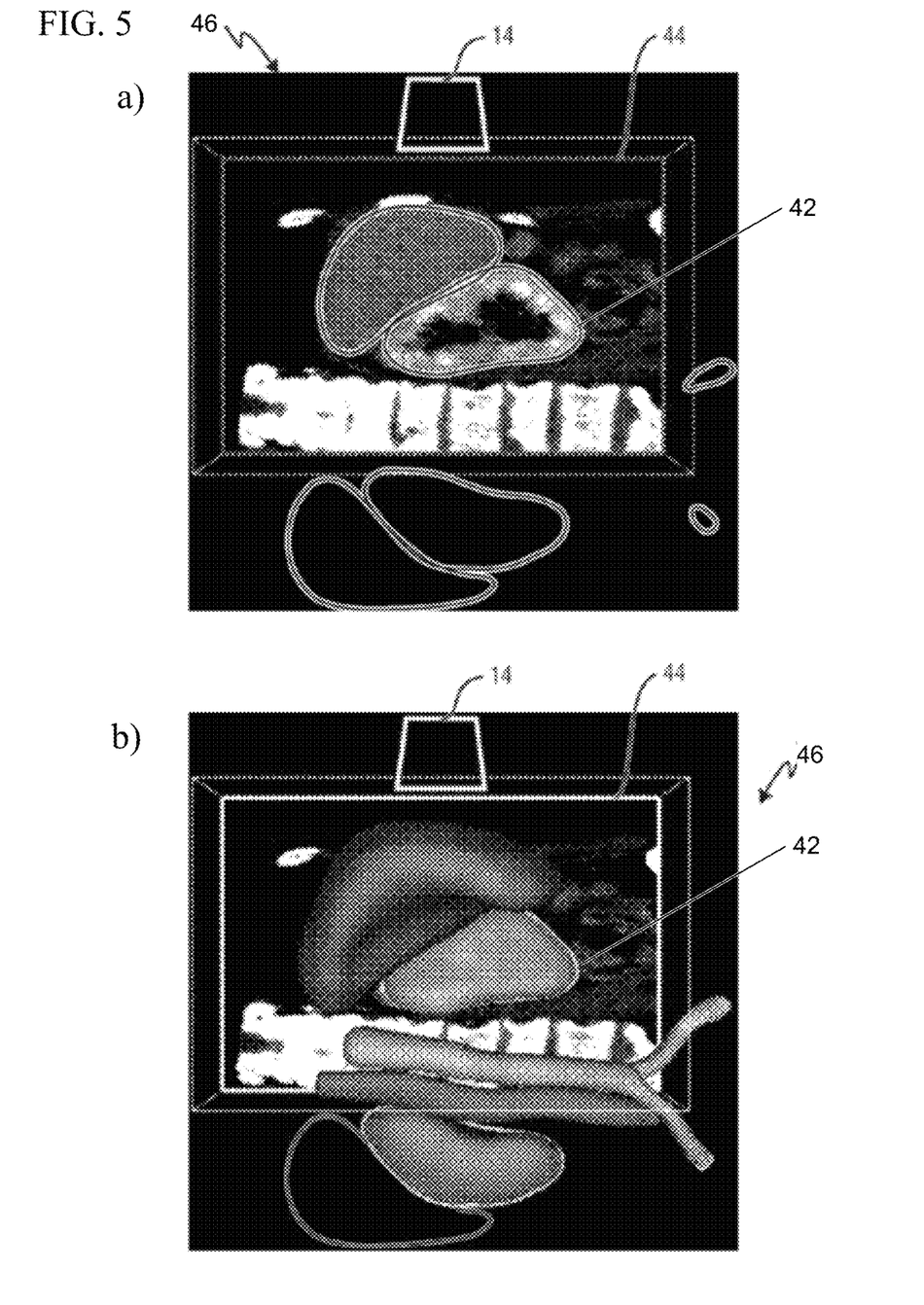

FIGS. 5*a, b* show the pre-operative medical image data 40 and the segmentation data 42 of the organs in different views. In FIG. 5*a*, the outer shape of the organs within the field of view 44 are superposed with a two-dimensional slice of the medical image data 40 to show the correlation of the organs as the anatomical objects of the segmentation data 42 and the organs of the ultrasound image data 46. In FIG. 5*b*, a three-dimensional representation of the segmentation data 42 is shown corresponding to the pre-operative medical image data 40 overlaid on the ultrasound image data 46.

Figure 6:
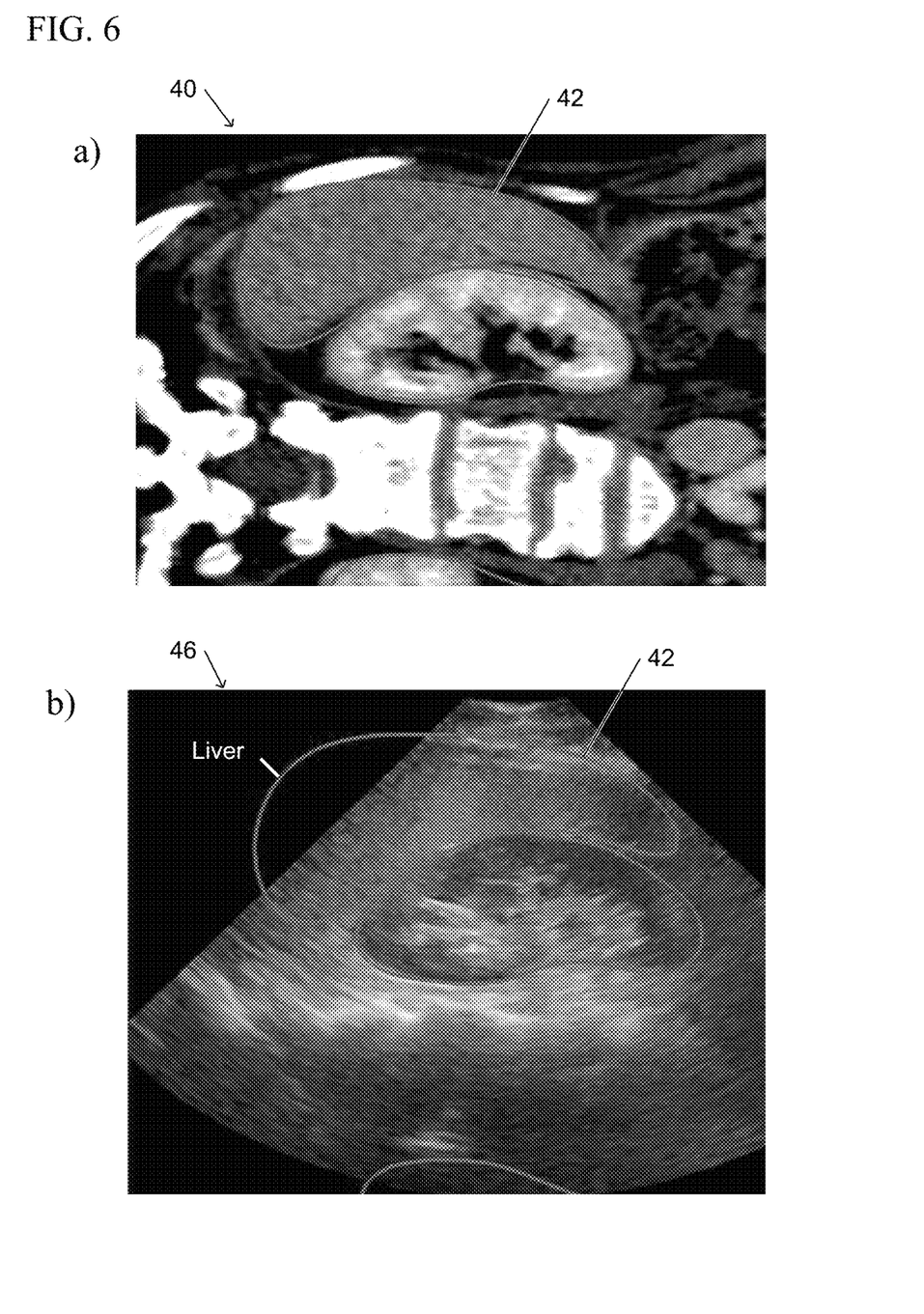

FIG. 6 show the segmentation data 42 with the corresponding medical image data 40 (FIG. 6*a*) and a correlation or a synchronization of the segmentation data 42 with the corresponding anatomical objects in the ultrasound image 46 (FIG. 6*b*) acquired by the ultrasound probe 14. In FIG. 6*b*, the outer shape of the organs within the field of view 44 are superposed upon a two-dimensional slice of the ultrasound image data 46 in order to identify the organs as the anatomical objects within the ultrasound image data 46. The outer shapes of the organs are derived from the segmentation data 42. The ultrasound image data 46 may also be superposed by a three-dimensional representation of the segmentation data 42 as shown in FIG. 5*b*. The correlation or a synchronization of the segmentation data 42 with the corresponding anatomical objects in the ultrasound image data 46 is achieved on the basis of the position of the probe 14 determined by the position determining unit 26.

In a certain embodiment, the respectively identified organs are labeled on the basis of the segmentation data 42 in order to show the operator which organs are present in the field of view 44.

Figure 7:
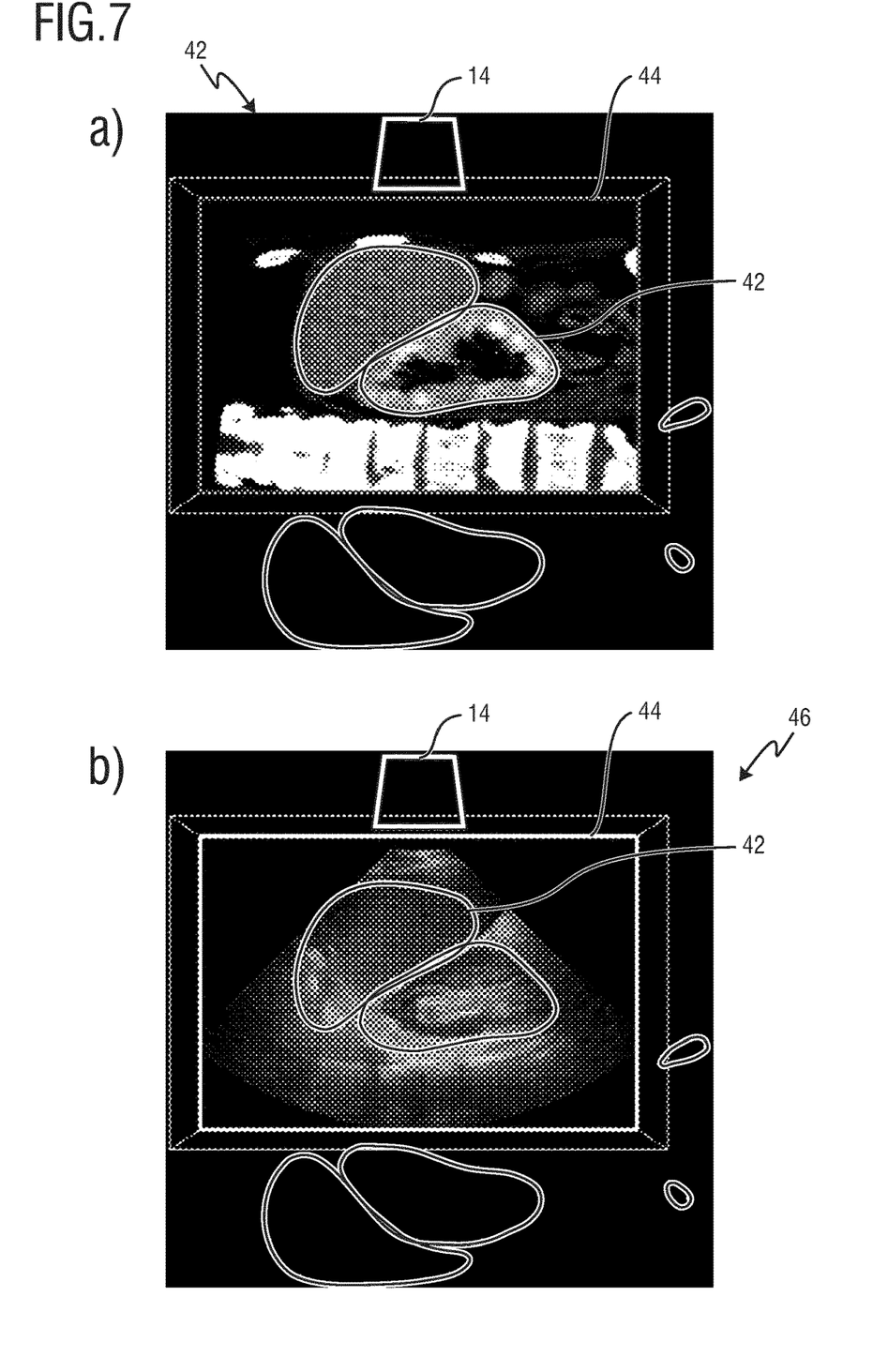

In FIG. 7 *a, b* a comparison of the pre-operative medical image data 40 including the corresponding segmentation data 42 and a misaligned segmentation data 42 with respect to the ultrasound image data 46 is shown. FIG. 7 *a* is identical with FIG. 5*a*. As shown in FIG. 7 *b*, the superposed outlines of the organs derived from the segmentation data 42 are misaligned with respect to the ultrasound data 46. The misalignment may occur due to a deviation of the determined position of the probe 14 to the actual position of the probe 14. In the case that a misalignment between the segmentation data 42 and the ultrasound image data 46 is detected, a recalibration of the position determining unit 26 can be performed automatically or manually upon request by the operator. In that case the position of the probe 14 is again calibrated on the basis of anatomical features of the patient 12 as mentioned above.

In the examples shown in FIG. 5*a,b* or 7*a,b*, the liver and one kidney are located within the field of view 44 of the ultrasound probe 14 and one kidney and the spleen is outside the field of view 44. In order to determine which organ is within the field of view 44, each 3D voxel of the ultrasound image data 46 or each pixel of the ultrasound data 46 is labeled, dedicated or assigned on the basis of the segmentation data and the position of the ultrasound probe 14 as a voxel or pixel of one certain organ or other tissue so that the amount of visible anatomical objects or organs can be easily determined by determining the amount of the respective voxels or pixels within the field of view 44. Therefore a volume or an area corresponding to the respective anatomical objects or organs can be calculated and displayed on the display screen 32.

Therefore, a percentage of the visible anatomical objects or organs can be computed and displayed on the display screen 32 either on the basis of the volume within the field of view 44 or the respective two-dimensional area within the two-dimensional slice displayed on the display screen 32.

Figure 8:
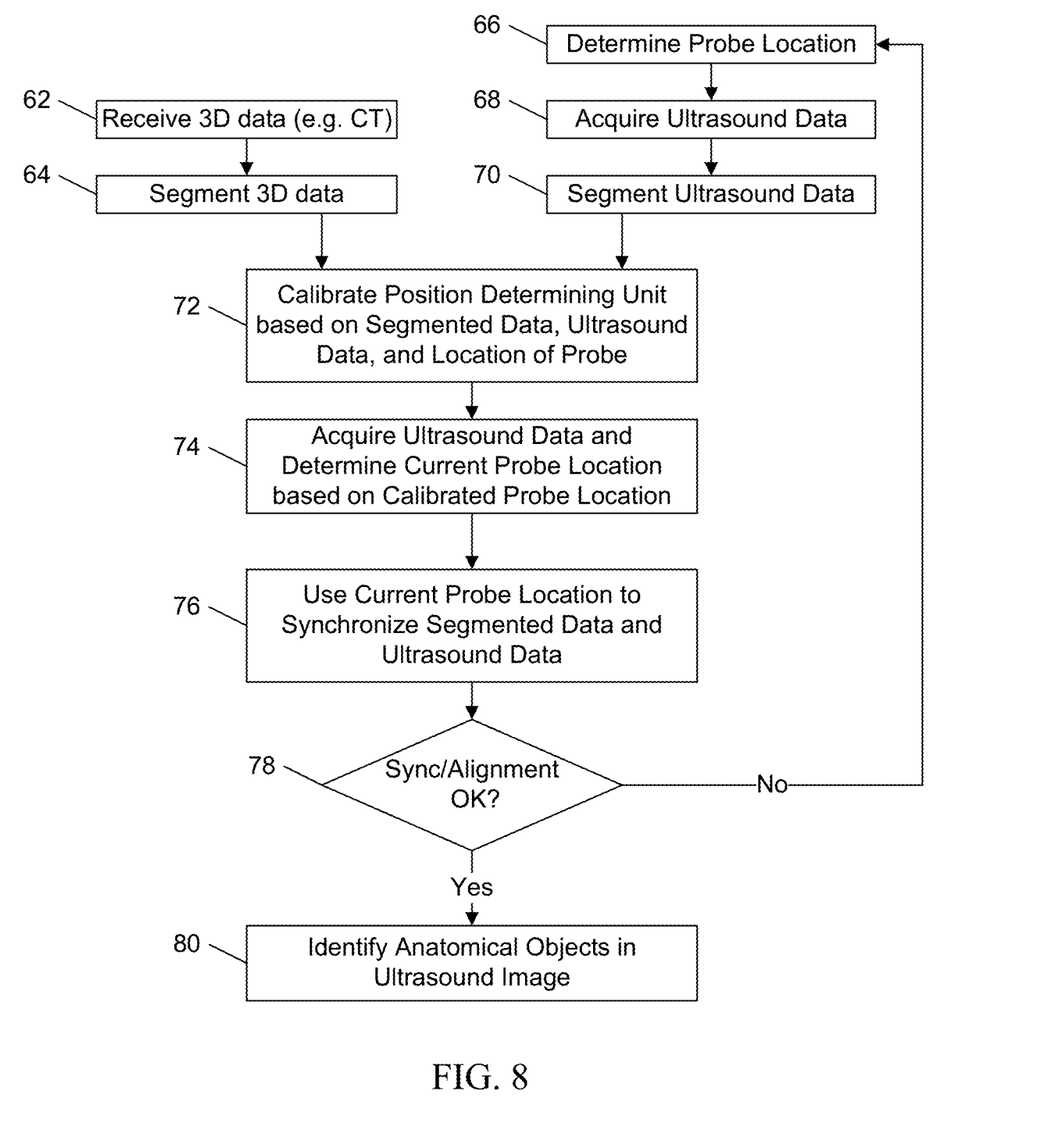
FIG. 8 shows a flow diagram of a method for correlating medical images.

In FIG. 8 a flow diagram of a method for identifying anatomical objects in a field of view of the ultrasound probe 14 is shown and generally denoted by 60.

The method 60 starts with receiving the 3D medical image data 40 as shown at step 62 followed by the segmentation of the 3D medical image data 40 as shown at step 64.

Further the position of the ultrasound probe 14 is determined by the position determining unit 26 as shown at step 66. At step 68, the ultrasound probe 14 acquires the ultrasound image data 46 and the so acquired ultrasound image data 46 is segmented at step 70 in order to determine the anatomical features 48 within the ultrasound image data 46.

At step 72, the position determining unit 26 is calibrated on the basis of the segmentation data 42, the ultrasound image data 46 and the position of the ultrasound probe 14 determined by the position determining unit 26.

At step 74, ultrasound image data 46 is captured or acquired and the current position of the ultrasound probe 14 is determined on the basis of the calibration of step 72 and in step 76 the ultrasound image data 46 and the segmentation data 42 are synchronized on the basis of the position of the probe 14.

In step 78 the synchronization of the ultrasound image data 46 and the segmentation data 42 is checked and if the respective anatomical objects are well aligned, the anatomical objects are identified in step 80. If the anatomical objects are not well aligned, the method returns to step 66 and determines the position of the ultrasound probe 14 and acquires an additional ultrasound image as shown at step 68.

By means of this method the anatomical objects within the field of view 44 can be identified with low time consumption and a high reliability since the position determining unit 26 can be precisely calibrated.

While the invention has been illustrated and described in detail in the drawings and foregoing description, such illustrations and descriptions are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An ultrasound imaging apparatus for identifying anatomical objects in a field of view, comprising:
   an image interface circuit that receives previously-acquired 3D medical image data of a patient,
   a segmentation circuit that segments anatomical objects of the patient in the previously-acquired 3D medical image data and provides first segmentation data of the anatomical objects,
   an ultrasound acquisition circuit that uses an ultrasound probe to acquire ultrasound data of the patient,
      wherein the segmentation circuit segments the anatomical objects of the patient in the ultrasound data and provides second segmentation data of the anatomical objects,
   a position determining circuit,
      wherein the position determining circuit determines a calibrated position of the ultrasound probe based on common anatomic features in the first segmented data and in the second segmented data, and
      wherein the position determining circuit determines a current position of the ultrasound probe based on detected movement of the ultrasound probe relative to the calibrated position,
   an identification circuit that identifies the anatomical objects in the ultrasound data of the patient on the basis of the first segmentation data of the anatomic objects and the current position of the ultrasound probe, and
   a display that displays an ultrasound image based on the ultrasound data and a representation of the identified anatomic objects.

2. The ultrasound imaging apparatus as claimed in claim 1, wherein the ultrasound acquisition circuit is adapted to determine 3D ultrasound data.

3. The ultrasound imaging apparatus as claimed in claim 2, wherein the identification circuit is adapted to identify the anatomical objects on the basis of a correlation of the anatomical features in the first and second segmentation data.

4. The ultrasound imaging apparatus as claimed in claim 2, wherein the calibration circuit is adapted to calibrate the calibrated position on the basis of a correlation of anatomical features in the first and second segmentation data.

5. The ultrasound imaging apparatus as claimed in claim 1, wherein the anatomical objects are organs of the patient.

6. The ultrasound imaging apparatus as claimed in claim 5, wherein a label of at least one of the identified organs is displayed by the display.

7. The ultrasound imaging apparatus as claimed in claim 1, wherein the calibration circuit is further adapted to re-determine the calibrated position of the ultrasound probe upon a request of an operator.

8. The ultrasound imaging apparatus as claimed in claim 6, wherein the calibration circuit is further adapted to re-determine the calibrated position of the ultrasound probe on the basis of the anatomical features in the first and second segmentation data when a misalignment is detected.

9. The ultrasound imaging apparatus as claimed in claim 2, wherein the acquired 3D ultrasound data comprises a plurality of 3D voxels, and wherein the 3D voxels are assigned to the corresponding anatomical objects of the segmentation data.

10. The ultrasound imaging apparatus as claimed in claim 9, wherein an anatomical object is identified in the field of view on the basis of an amount of 3D voxels of the anatomical object in the field of view.

11. The ultrasound imaging apparatus as claimed in claim 1, wherein the ultrasound acquisition circuit is adapted to acquire 2D ultrasound data.

12. The ultrasound imaging apparatus as claimed in claim 11, wherein the acquired 2D ultrasound data comprises a plurality of 2D pixels assigned to the corresponding anatomical objects of the segmentation data, wherein an anatomical object is identified in the ultrasound data on the basis of an amount of 2D pixels of the anatomical object in the ultrasound data.

13. A method for identifying anatomical objects in a field of view of an ultrasound acquisition unit, comprising the steps of:
   receiving previously-acquired 3D medical image data of a patient,
   segmenting anatomical objects in the previously-acquired 3D medical image data and providing first segmentation data of the anatomical objects,
   acquiring ultrasound data of the patient by means of an ultrasound probe of the ultrasound acquisition unit,
   segmenting the anatomical objects in the ultrasound data and providing second segmentation data of the anatomical objects,
   determining a calibrated position of the ultrasound probe on the basis of the first and second segmentation data of the anatomical objects of the patient,
   determining a current position of the ultrasound probe with respect to the calibrated position of the ultrasound probe based on movement of the ultrasound probe,
   identifying the anatomical objects within the field of view on the basis of the first segmentation data and the current position of the probe and,
   displaying the ultrasound data and an identification of the anatomic objects within the field of view.

14. A non-transitory computer-readable medium comprising a program that, when executed by a processor circuit, causes the processor circuit to:
receive previously-acquired 3D medical image data of a patient,
segment anatomical objects in the previously-acquired 3D medical image data to provide first segmentation data of the anatomical objects,
acquire ultrasound data of the patient by means of an ultrasound probe of the ultrasound acquisition unit,
segment anatomical objects in the ultrasound data to provide second segmentation data of the anatomical objects,
determine a calibrated position of the ultrasound probe on the basis of the first and second segmentation data of the anatomical objects of the patient,
determine a current position of the ultrasound probe with respect to the calibrated position of the ultrasound probe based on detected movement of the ultrasound probe,
create an ultrasound image based on the ultrasound data,
identify the anatomical objects within the ultrasound image on the basis of the first segmentation data and the current position of the probe, and
display the ultrasound image with and identification of the anatomic objects within the ultrasound image.

15. The medium of claim 14, wherein the ultrasound data comprises 3D ultrasound data.

16. The medium of claim 14, wherein the program causes the processing circuit to determine the calibrated position of the ultrasound probe based on a correlation of anatomical features in the first and second segmentation data.

17. The medium of claim 14, wherein the anatomical objects are organs of the patient.

18. The medium of claim 14, wherein the program causes the processing circuit to display a label that identifies at least one organ of the patient.

19. The medium of claim 14, wherein the program causes the processing circuit to re-determine the calibrated position of the ultrasound probe when a misalignment of the ultrasound image and the identification of the anatomic objects is detected.

20. The medium of claim 14, wherein the program causes the processing circuit to identify the anatomical objects based on a correlation of a determined volume of the anatomic object in each of the segmentation data and the ultrasound data.

21. An ultrasound imaging apparatus for identifying anatomical objects in a field of view, comprising:
an image interface unit that receives previously-acquired 3D medical image data of a patient,
a segmentation unit that segments anatomical objects of the patient in the previously-acquired 3D medical image data and provides first segmentation data of the anatomical objects,
an ultrasound acquisition unit that uses an ultrasound probe to acquire ultrasound data of the patient,
wherein the segmentation unit segments the anatomical objects of the patient in the ultrasound data and provides second segmentation data of the anatomical objects
a position determining unit,
wherein the position determining unit determines a calibrated position of the ultrasound probe based on common anatomic features in the first segmented data and in the second segmented data, and
wherein the position determining unit determines a current position of the ultrasound probe based on detected movement of the ultrasound probe relative to the calibrated position,
an identification unit that identifies the anatomical objects in the ultrasound data of the patient on the basis of the first segmentation data of the anatomic objects and the current position of the ultrasound probe, and
a display that displays an ultrasound image based on the ultrasound data and a representation of the identified anatomic objects.

22. An ultrasound imaging apparatus for identifying anatomical objects in a field of view, comprising:
an image interface for receiving previously-acquired 3D medical image data of a patient,
a segmentation unit for segmenting anatomical objects of the patient in the previously-acquired 3D medical image data and for providing segmentation data of the anatomical objects,
an ultrasound acquisition unit including an ultrasound probe for acquiring ultrasound data of the patient,
a position determining unit for determining a current position of the ultrasound probe with respect to a calibrated position,
wherein the position determining unit includes a calibration unit adapted to determine the calibrated position on the basis of anatomical features in the ultrasound data of the patient acquired at an initial position of the ultrasound probe and the segmentation data, such that the initial position of the ultrasound probe is determined with respect to the segmentation data, and
an identification unit for identifying the anatomical objects within the field of view of the ultrasound probe on the basis of the segmentation data and the current position of the ultrasound probe with respect to the calibrated position,
wherein, when a misalignment between the segmentation data and the acquired ultrasound data of the patient is detected, the calibration unit is further adapted to calibrate the current position of the ultrasound probe on the basis of the anatomical features in the ultrasound data of the patient acquired at the current position of the ultrasound probe and the segmentation data.

* * * * *